(12) United States Patent
Komuro et al.

(10) Patent No.: US 7,402,648 B2
(45) Date of Patent: Jul. 22, 2008

(54) METHOD FOR PRODUCING CYCLIC ORGANIC SILICON COMPOUND AND ORGANIC SILICON RESIN HAVING ALCOHOLIC HYDROXYL GROUP

(75) Inventors: Katsuhiko Komuro, Utsunomiya (JP); Hiroshi Suzuki, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 122 days.

(21) Appl. No.: 10/577,948

(22) PCT Filed: Nov. 5, 2004

(86) PCT No.: PCT/JP2004/016445

§ 371 (c)(1),
(2), (4) Date: Sep. 11, 2006

(87) PCT Pub. No.: WO2005/044828

PCT Pub. Date: May 19, 2005

(65) Prior Publication Data

US 2007/0055036 A1    Mar. 8, 2007

(30) Foreign Application Priority Data

Nov. 17, 2003  (JP) ............................. 2003-377752
Feb. 16, 2004  (JP) ............................. 2004-039063

(51) Int. Cl.
   *C08G 77/04*   (2006.01)
(52) U.S. Cl. ......................... 528/37; 556/464
(58) Field of Classification Search ............... 528/37; 556/464
   See application file for complete search history.

(56) References Cited

U.S. PATENT DOCUMENTS 3,539,610 A * 11/1970 Abe ........................... 556/427

(Continued)

FOREIGN PATENT DOCUMENTS

| JP | 7 149901 | 6/1995 |
| JP | 8 231924 | 9/1996 |
| JP | 9 176321 | 7/1997 |
| JP | 10 87834 | 4/1998 |
| JP | 11 116681 | 4/1999 |
| JP | 2001 213963 | 8/2001 |
| JP | 2002 249493 | 9/2002 |
| JP | 2002 338583 | 11/2002 |
| JP | 2003 98670 | 4/2003 |
| JP | 2003 146832 | 5/2003 |
| JP | 2003 149822 | 5/2003 |

OTHER PUBLICATIONS

Trost et al., "Markovnikov Alkyne Hydrosilylation Catalyzed by Ruthenium Complexes", Journal of the American Chemical Society, vol. 123, No. 50, pp. 12726-12727, 2001.

(Continued)

*Primary Examiner*—Randy Gulakowski
*Assistant Examiner*—Robert Loewe
(74) *Attorney, Agent, or Firm*—Oblon, Spivak, McClelland, Maier & Neustadt, P.C.

(57) ABSTRACT

The object of the present invention is to provide a production method wherein synthesis of a cyclic organic silicon compound similar to oxa-silacyclopentanes is completed in a single-step reaction. It is also to provide an organic silicon resin having an alcoholic hydroxyl group, which is capable of easily controlling its construction and is longitudinally stable.

The means for solving is to produce the cyclic organic silicon compound represented by the formula (3) below by reacting an olefin represented by the formula (1) below and an alkoxysilane represented by the formula (2) below in the presence of a catalyst comprising a transition metal.

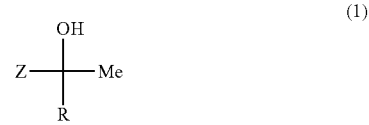

(In the formula, Z is alkenyl group having carbon atoms from 2 to 5 where the terminal carbon atom forms a C=C bond, R is methyl group or hydrogen atom, and Me is methyl group.)

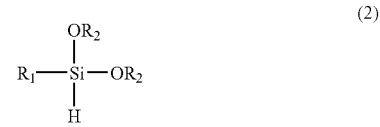

(In the formula, $R_1$ is alkyl group or alkoxyl group, having carbon atoms from 1 to 3, and $R_2$ is alkyl group having carbon atoms from 1 to 3.)

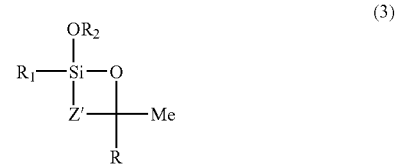

(In the formula, Z' is alkylene group having carbon atoms from 2 to 5.)

And it is an organic silicon resin having an alcoholic hydroxyl group obtained by performing hydrolysis and condensation of a cyclic organic silicon compound represented by the formula (3) above, or of a mixture of this and a polyfunctional alkoxysilane.

3 Claims, 5 Drawing Sheets

U.S. PATENT DOCUMENTS

| | | | | |
|---|---|---|---|---|
| 4,924,021 | A | * | 5/1990 | Kotzsch et al. .............. 556/464 |
| 5,124,468 | A | * | 6/1992 | Krafft et al. ................. 556/436 |
| 5,191,102 | A | * | 3/1993 | Oyama et al. ............... 556/464 |
| 5,520,767 | A | * | 5/1996 | Larson .................... 156/307.5 |
| 5,595,593 | A | * | 1/1997 | Burns et al. ................. 106/499 |
| 5,856,392 | A | * | 1/1999 | Kennedy et al. ............ 525/479 |
| 5,861,468 | A | * | 1/1999 | Harkness et al. ............. 528/19 |
| 6,774,202 | B2 | * | 8/2004 | Lee ............................. 528/33 |
| 2004/0082681 | A1 | * | 4/2004 | Brand et al. .................. 522/99 |
| 2007/0184006 | A1 | * | 8/2006 | Ferenz et al. ............ 424/70.12 |

OTHER PUBLICATIONS

Walkup et al., "Effects of Variations of Alkoxy Substituents Upon Cyclizations of Dialkoxy-2-Chloroethylsilyl Enol Ethers to Form 2,2-Dialkoxy-1-Oxa-2-Silacyclohexanes[1]", Chemistry Letters, No. 7, pp. 1055-1058, 1990.

Tanino et al., "Control of Stereochemistry by σ-Participation of a Silyl Group. A Novel Method for Diastereoselective Polyol Synthesis", J. Org. Chem., vol. 62, pp. 4206-4207, 1997.

Bear et al., "Diastereoselective Nucleophilic Substitution Reactions of Oxasilacyclopentane Acetals: Application of the "Inside Attack" Model for Reactions of Five-Membered Ring Oxocarbenium Ions", J. Org. Chem., vol. 67, pp. 2056-2064, 2002.

Rossmy et al., "1,2-Siloxacycloalkane- 1. Mitt. Synthese und Polymerisationsverhalten", Makromolekulare Chemie, vol. 73, pp. 85-108, 1964.

Koerner et al., 1,2-Siloxacycloalkane- 2. Mitt Synthese und Chemisches Verhalten Von 1,1'-DI-(1-Methyl-1,2-Siloxacyclopentyl)-Oxid*, Makromolekulare Chemie, vol. 97, pp. 241-247, 1996.

* cited by examiner

METHOD FOR PRODUCING CYCLIC ORGANIC SILICON COMPOUND AND ORGANIC SILICON RESIN HAVING ALCOHOLIC HYDROXYL GROUP

TECHNICAL FIELD

The present invention relates to a method for producing a cyclic organic silicon compound. More particularly, it relates to a method for producing an alkoxysilane having a hydroxyl group, protected by an organic substituent group.

The present invention also relates to a novel organic silicon-based resin having an alcoholic hydroxyl group, and to a method for producing the same.

The organic silicon-based resin of the present invention is useful as a starting material for lithographic material, organic-inorganic hybrid material and the like.

BACKGROUND ART (Cyclic Organic Silicon-based Compound)

Numerous compounds are known as halogenosilanes and alkoxysilanes, having a protected alkali-soluble group. The protected alkali-soluble group includes carboxyl group and protected hydroxyl group in phenol, catechol (for example in Patent Document 1 and Patent Document 2) or alcohol.

Halogenosilanes and alkoxysilanes, having an alkali-soluble group are useful as a starting material for lithographic material, organic-inorganic hybrid material and the like.

[Patent Document 1] JP-A-2002-249493

[Patent Document 2] JP-A-2002-338583

However, known methods for producing halogenosilanes and alkoxysilanes, having an alkali-soluble group until now have used multi-step synthesis reactions, and are therefore impractical as methods for low-cost manufacturing.

On the other hand, oxa-silacyclopentanes are known as a cyclic organic silicon compound having a hydroxyl group protected by an organic group (for example in Non-patent Document 1 and Non-patent Document 2).

[Non-patent Document 1] J. Org. Chem. 1997, 62, 4206-4207

[Non-patent Document 2] J. Org. Chem. 2002, 67, 2056-2064

It is also known that oxa-silacyclopentanes easily ring-opening react by hydrolysis to form a silicon-based resin having an alcoholic hydroxyl group (for example in Non-patent Document 3 and Non-patent Document 4).

[Non-patent Document 3] MakromolekulareChemie 1964, 73, 85

[Non-patent Document 4] MakromolekulareChemie 1966, 97, 241

(Organic Silicon Resin Having Alcoholic Hydroxyl Group)

Various types of organic silicon resins having an alcoholic hydroxyl group are known. The conventional organic silicon resin is one obtained by introducing an alcoholic hydroxyl group into an organic silicon resin constituting a backbone of the polymer.

[Patent Document 1] JP-A-H08-231924

[Patent Document 2] JP-A-H09-176321

[Patent Document 3] JP-A-2001-213963

[Patent Document 4] JP-A-2003-146832

Since these conventional organic silicon resins are obtained by a polymer reaction whereby a specific reactive group in the polymer is reacted with a compound having an alcoholic hydroxyl group, it is difficult to precisely control an introduced amount of the alcoholic hydroxyl group, and when starting materials remain after the polymer reaction, it is difficult to remove the starting materials and purify an organic silicon resin.

A method whereby an organic silicon resin having an alicyclic epoxide is synthesized, and then an oxidation reaction (polymer reaction) is used to convert the product to an organic silicon resin having a diol has been proposed as a method for obtaining a silicon resin having an alcoholic hydroxyl group (for example in Patent Document 5).

[Patent Document 5] JP-A-H10-87834

In addition, a polymethylsilsesquioxane-based microparticle having an alcoholic hydroxyl group has been reported (for example in Patent Document 6).

[Patent Document 6] JP-A-H11-116681

Since an organic silicon resin having an alcoholic hydroxyl group produces an alkali-soluble group, and it is useful as a starting material for lithographic material, organic-inorganic hybrid material and the like.

[Patent Document 7] JP-A-2003-149822

These resins can also be a starting material for various types of functional materials, since they easily react with a silylating agent.

On the other hand, it has been reported that oxa-silacyclopentanes are useful as intermediates in organic synthesis.

[Non-patent Document 1] J. Org. Chem. 1997, 62, 4206

[Non-patent Document 2] J. Org. Chem. 2002, 67, 2056

Moreover, basic researches have also been conducted on oxa-silacyclopentane since it easily ring-opening reacts by hydrolysis to give a hydroxyl group.

[Non-patent Document 3] MakromolekulareChemie 1964, 73, 85

[Non-patent Document 4] MakromolekulareChemie 1966, 97, 241

DISCLOSURE OF THE INVENTION

Problems to be Solved by the Invention

A ring-opening reaction of an oxa-silacyclopentane leads to an alcoholic hydroxyl group, and the oxa-silacyclopentane is therefore useful as various intermediates and reactants in organic synthesis, and starting materials for resin.

However, at least a two-stage reaction that includes 1) hydrosilylation of an olefin and a hydrosilane, and 2) a ring-closing reaction are necessarily performed in order to synthesize an oxa-silacyclopentane, and some compounds require a reaction process having two or more steps.

An object of the present invention is to provide a method whereby synthesis of a cyclic organic silicon compound having the same structure as an oxa-silacyclopentane is completed by a single-step reaction, and the desired compound is obtained with high purity and high yield.

In addition, as described above, many reports include methods utilized a polymer reaction for the purpose of introducing an alcoholic hydroxyl group into an organic silicon resin, and it is extremely difficult to control the construction of the resin precisely.

The alcoholic hydroxyl group is prone to react with a silanol remaining in the resin, and an organic silicon resin having an alcoholic hydroxyl group also gels easily.

Another object of the present invention is to devise a stable organic silicon resin having an alcoholic hydroxyl group, which is capable of easily controlling its construction and does not change with time, and a production method thereof.

Means for Solving Problems

The present invention relates to invention 1 (hereinafter abbreviated as "present invention 1") involving a method for producing a cyclic organic silicon compound, and to invention 2 (hereinafter abbreviated as "present invention 2") involving an organic silicon resin having an alcoholic hydroxyl group.

The production method of the present invention 1 is a method for producing a cyclic organic silicon compound represented by the general formula (3) below, where it is characterized in that an olefin represented by the general formula (1) below and an alkoxysilane represented by the general formula (2) below are reacted in the presence of a catalyst comprising a transition metal.

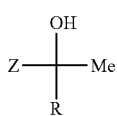
(1)

(In the formula, Z is alkenyl group having carbon atoms from 2 to 5 where the terminal carbon atom $C_E$ distant from the carbon atom to which the hydroxyl group is bonded forms a carbon-carbon unsaturated bond, R is methyl group or hydrogen atom, and Me is methyl group.)

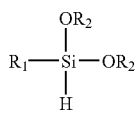
(2)

(In the formula, $R_1$ is alkyl group or alkoxyl group, having carbon atoms from 1 to 3, $R_2$ is alkyl group having carbon atoms from 1 to 3, and the plurality of $R_2$ may be the same as or different from each other.)

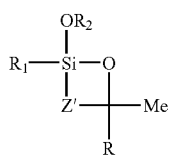
(3)

(In the formula, Z' is alkylene group having carbon atoms from 2 to 5, wherein the carbon-carbon unsaturated bond in Z transformed into a saturated bond and the terminal carbon atom $C_E$ in Z binds to Si atom; R is methyl group or hydrogen atom; $R_1$ is alkyl group or alkoxyl group, having carbon atoms from 1 to 3; and $R_2$ is alkyl group having carbon atoms from 1 to 3.)

The present invention 2 provides a stable organic silicon resin having an alcoholic hydroxyl group, which is capable of easily controlling its construction and does not change with time, by using a cyclic organic silicon compound such as oxa-silacyclopentane as a starting material for the resin.

The organic silicon resin of the present invention 2 is an organic silicon resin having an alcoholic hydroxyl group, which is obtained by performing hydrolysis and condensation of a cyclic organic silicon compound represented by the general formula (3) above (hereinafter abbreviated as "cyclic organic silicon compound [3]"), or of a mixture of this and a polyfunctional alkoxysilane.

The preferable starting compound is a cyclic organic silicon compound (hereinafter, abbreviated as "DESMBO") having substituent groups as shown below in the general formula (3) described above, considering the availability and the cost of the starting material.

Z': ethylene group
R: methyl group
$R_1$: ethoxy group
$R_2$: ethyl group

Hydrolysis and condensation of this compound lead readily to a stable organic silicon resin having an alcoholic hydroxyl group, which is capable of easily controlling its construction and does not change with time.

The preferable production method for obtaining the organic silicon resin of the present invention 2 is one including hydrolysis and condensation of a cyclic organic silicon compound [3], or of a mixture of this compound and a polyfunctional alkoxysilane in an organic solvent while maintaining a concentration of a producing polymer at 30% by weight or less.

The preferable production method is consisted of four steps described below.

Step (1): The cyclic organic silicon compound or a mixture of this compound and a polyfunctional alkoxysilane is hydrolyzed in an organic solvent, an organic solvent is furthermore added, and a dehydrating agent is then added to dehydrate.

Step (2): The dehydrating agent is filtered, and then the terminal silanol of the resin is terminated using a silylating agent.

Step (3): The solvent is distilled, and then an organic solvent and water are added to rinse the organic silicon resin having an alcoholic hydroxyl group.

Step (4): A dehydrating agent is added to dehydrate for the resin, and then the solvent is distilled to obtain an organic silicon resin having an alcoholic hydroxyl group.

Effects of the Invention

According to the present invention 1, a cyclic organic silicon compound having an alcoholic hydroxyl group and an alkoxyl group, protected by an organic substituent group can be synthesized by a single-step reaction.

In addition, according to the method of the present invention 1, secondary reactions can be suppressed, and the desired cyclic organic silicon compound can be obtained with high purity and high yield.

In the case of producing an oxa-silacyclopentane, a product having a purity of 98% or higher easily be obtained.

The cyclic organic silicon compound obtained by the present invention 1, having an alkoxysilyl group, can form a siloxane bond by reacting with another organic silicon compound (including polymers) and induce a coupling reaction with a silanol group in an inorganic compound.

Furthermore, the cyclic organic silicon compound obtained by the present invention 1 is easily ring-opened by a hydrolysis reaction to form an alcoholic hydroxyl group, and this alcoholic hydroxyl group functions as an alkali-soluble group and a cross-linkable group. Specifically, this compound functions as a co-reactive silicon compound having a silicon functional group and a protected carbon-functional group.

The cyclic organic silicon compound obtained by the production method of the present invention is therefore useful as an intermediate in organic synthesis, a starting material for resin synthesis, a resin modifier, and a surface-treating agent for inorganic compounds.

According to the present invention 2, a stable organic silicon resin having an alcoholic hydroxyl group, which is capable of easily controlling its construction and does not change with time can be obtained.

According to the production method of the present invention 2, a production of an organic silicon resin having an alcoholic hydroxyl group can be stably proceded without changing its molecular weight while conducting to controlling its construction easily.

BEST MODE FOR CARRYING OUT THE INVENTION

The present invention 1 relates to a method for producing the cyclic organic silicon compound represented by the general formula (3) above. Hereinafter, the present invention 1 will be described in detail.

The cyclic organic silicon compound represented by the general formula (3) above can be synthesized by performing a hydrosilylation reaction and a ring-closing condensation reaction (dealcoholization reaction) of an olefin (1) having a hydroxyl group and an alkoxysilane (2) in the presence of a catalyst comprising a transition metal.

Since these reactions can be performed instantaneously according to the present invention 1, almost no secondary reactions occur, and the desired compound can be obtained with extremely high purity and high yield.

Olefin Having Hydroxyl Group

The olefin having a hydroxyl group is represented by the general formula (1) below.

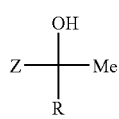

(1)

In the formula, Z is an alkenyl group having carbon atoms form 2 to 5 where the terminal carbon atom $C_E$ distant from the carbon atom to which the hydroxyl group is bonded forms a carbon-carbon unsaturated bond, R is a methyl group or a hydrogen atom, preferably a methyl group, and Me is a methyl group.

Examples of the preferable olefin include 1-propene-3-methyl-3-ol, 1-butene-4-methyl-4-ol, 1-pentene-5-methyl-5-ol, 1-hexene-6-methyl-6-ol, 1-butene-3-methyl-3-ol, 1-pentene-4-methyl-4-ol, 1-hexene-5-methyl-5-ol and 1-heptene-6-methyl-6-ol.

Among these, 1-butene-3-methyl-3-ol is most preferred since it is easily obtained as a starting material.

When a compound having no methyl groups at α-position of the hydroxyl group is used as the olefin (1), large quantities of byproducts are generated, and the yield of the desired compound is significantly reduced.

Alkoxysilane

The alkoxysilane is represented by the general formula (2) below.

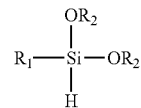

(2)

(In the formula, $R_1$ is an alkyl group or an alkoxyl group, having carbon atoms from 1 to 3, $R_2$ is an alkyl group having carbon atoms from 1 to 3, and the plurality of $R_2$ may be the same as or different from each other.)

Examples of the preferable alkoxysilane include trimethoxysilane, triethoxysilane, tripropoxysilane, methyldimethoxysilane, methyldiethoxysilane, methyldipropoxysilane, methoxydiethoxysilane, methoxydipropoxysilane, ethoxydipropoxysilane, methylmethoxyethoxysilane, methylmethoxypropoxysilane and the like. Among these, triethoxysilane in which $R_1$ is an ethoxy group and $R_2$ is an ethyl group is most preferred.

Catalyst

A hydrosilylation reaction and a ring-closing condensation reaction (dealcoholization reaction) of an olefin represented by the general formula (1) above and an alkoxysilane represented by the general formula (2) above in the presence of a catalyst comprising a transition metal are performed.

The catalyst used in the present invention 1 is not particularly limited insofar as it is known to accelerate the hydrosilylation reaction. Examples of the preferable catalyst includes an elemental metal of group 8 to group 10, such as cobalt, nickel, ruthenium, rhodium, palladium, iridium and platinum, an organic metal complex thereof, a metal salt thereof, a metal oxide thereof, and the like.

A platinum-based catalyst is usually used, and examples of the preferable platinum-based catalyst include platinic chloride hexahydrate ($H_2PtCl_6 \cdot 6H_2O$), cis-$PtCl_2(PhCN)_2$, platinum carbon, a platinum complex (Pt-dvds) in which a divinylsiloxane is coordinated, and the like. The symbol "Ph" indicates a phenyl group.

The amount of the catalyst used is preferably 0.1 ppm to 1,000 ppm with respect to the olefin represented by the general formula (1) above.

Reaction Conditions

The olefin (1) and the alkoxysilane (2) are preferably charged in a ratio whereby a compound having lower boiling point among these starting compounds comprises 110 to 120 moles based on 100 moles of a compound having higher boiling point.

This ratio is adopted in order to facilitate purification by distillation after synthesis.

Since the alkoxysilane (2) is usually a compound whose boiling point is lower than the olefin (1), an excess of the alkoxysilane (2) is usually used with respect to the olefin (1).

In addition, a reaction temperature can not be conditionally determined since the operation for controlling the reaction temperature depends on a heating condition from the outside and a charging rate of the alkoxysilane. Maintaining a reaction temperature in the range from 40 to 120° C. usually leads to the hydrosilylation reaction and the ring-closing condensation reaction (dealcoholization reaction) smoothly.

The product obtained by the above-mentioned reactions can be further purified through removal of the unreacted starting materials by an appropriately purification process including a distillation and the like to a purity of 90% or higher easily.

Hydrolysis and Condensation of Cyclic Organic Silicon Compound [3]

The cyclic organic silicon compound [3] synthesized as described above is hydrolyzed under acidic or basic condition to form an organic silicon resin backbone, and at the same time a hydroxyl group can be introduced into the resin backbone.

The product obtained by hydrolysis and condensation is a polymer having a repeating unit indicated below. Specifically, when $R_1$ in the general formula (3) above is an alkyl group having carbon atoms from 1 to 3, the repeating unit is represented by [A] below.

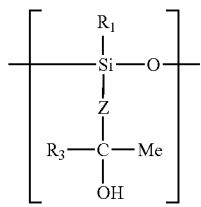

When $R_1$ in the general formula (3) above is an alkoxyl group having carbon atoms from 1 to 3, the repeating unit is represented by [B] below.

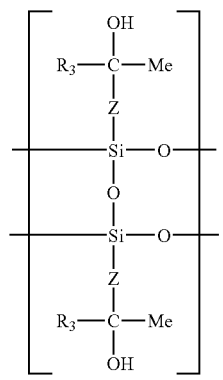

An essential feature of both the repeating units [A] and [B] is that the repeating units have a hydroxyl group produced by opening the ring of the cyclic organic silicon compound.

The organic silicon resin of the present invention includes the product obtained by hydrolysis and condensation of a cyclic organic silicon compound [3] alone, as well as the product obtained by hydrolysis and co-condensation of a mixture of a cyclic organic silicon compound [3] and a polyfunctional alkoxysilane.

The preferable polyfunctional alkoxysilane includes tri- to tetrafunctional alkoxysilanes, and a polyfunctional alkoxysilane composed of an alkyl group having carbon atoms from 1 to 3 and/or an alkoxy group having carbon atoms from 1 to 3 is preferred. Examples of preferable tri- to tetrafunctional alkoxysilane include triethoxysilane, tetraethoxysilane, methyltrimethoxysilane, methyltriethoxysilane and the like.

The preferable ratio of the polyfunctional alkoxysilane to the cyclic organic silicon compound [3] is 10 moles or less based on 1 mole of the cyclic organic silicon compound [3].

The preferable number-average molecular weight of the organic silicon-based resin of the present invention is in the range from 1,000 to 1,000,000, and the average molecular weight is more preferably from 1,000 to 100,000 as measured by GPC.

Examples of the preferable acid include hydrochloric acid, nitric acid, sulfuric acid, acetic acid, formic acid and the like.

Examples of the preferable base include sodium hydroxide, potassium hydroxide, lithium hydroxide, tetramethylammonium hydroxide, triethylamine, pyridine and the like.

The preferable amount of water used in hydrolysis is equal to or more than the theoretical quantity, and is preferably 1.5 to 2 times the theoretical quantity.

Examples of the preferable organic solvent used in hydrolysis include acetone, methanol, ethanol, isopropyl alcohol, methylethylketone, methylisobutylketone, propylene glycol monomethyl ether acetate, toluene, hexane and the like. These may be used singly or in combinations of two or more types thereof.

Examples of the preferable agent for adjusting molecular weight include hexamethyldisiloxane, tetramethyldisiloxane, hexaphenyldisiloxane, hexavinyldisiloxane, tetraphenyldimethyldisiloxane, tetraisopropyldisiloxane and the like.

Examples of a dehydrating agent used after hydrolysis include anhydrous sodium sulfate, anhydrous magnesium sulfate and the like. Type of the dehydrating agent is not particularly limited insofar as it has dehydrating effects and does not contaminate the resin.

The terminal silanol of the resin is terminated with a silylating agent. When the terminal silanol of the resin is terminated, an organic silicon resin having an alcoholic hydroxyl group, which is stable with time, can be produced.

Examples of the preferable silylating agent include 1,1,1,3,3,3-hexamethyldisilazane, 1,1,3,3-tetramethyldisilazane, heptamethyldisilazane, 1,3-divinyl-1,1,3,3-tetramethyldisilazane, 1,1,3,3,5,5-hexamethylcyclotrisilazane, tris(trimethylsilyl)amine, bis(diethylamino)dimethylsilane, bis(dimethylamino)dimethylsilane, bis(dimethylamino)diphenylsilane, bis(dimethylamino)methylphenylsilane, trimethylsilanol, t-butylaminotrimethylsilane, and other aminosilanes and silanols; and chlorosilanes such as trimethylchlorosilane, dimethylchlorosilane and phenylmethylchlorosilane. These may also be jointly used with a base such as triethylamine and pyridine.

The terminal silanol in the silicon-based resin obtained immediately after hydrolysis and condensation is terminated, and then the solvent is evaporated under reduced pressure. After that, an organic solvent is added and the organic silicon resin is rinsed.

Examples of the preferable organic solvent used in rinsing include acetone, methanol, ethanol, isopropyl alcohol, methylethylketone, methylisobutylketone, propylene glycol monomethyl ether acetate, toluene, hexane and the like. These may be used singly or in combinations of two or more types thereof.

Ultrapure water is generally used for rinsing, but it is also possible to use an acid aqueous solution such as aqueous solution of hydrochloric acid, a basic aqueous solution such as aqueous solution of sodium hydroxide, a saturated aqueous solution of sodium chloride, and the like. Rinsing is preferably performed until the water layer becomes neutral.

After rinsing, dehydration and evaporation of the solvent under reduced pressure is performed to obtain a stable organic silicon resin having an alcoholic hydroxyl group is obtained that has an easily controlled composition and does not change over time. Examples of a dehydrating agent used after rinsing include anhydrous sodium sulfate, anhydrous magnesium sulfate and the like. Type of the dehydrating agent is not particularly limited insofar as it has dehydrating effects and does not contaminate the resin.

EXAMPLES

Hereinafter, the present invention will be described in detail using Example.

Example 1

1-Butene-3-methyl-3-ol (30 g, 348 mmol) was charged into and stirred in a reaction vessel (flask) provided with a condenser, a dropping funnel and a magnetic stirrer and placed in an oil bath. Triethoxysilane (62.9 g, 383 mmol) was incorporated into the dropping funnel. The triethoxysilane (11.2 mL) in the dropping funnel was added into the flask, and the temperature of the oil bath was set to 80° C. When the internal temperature reached 70° C., a 0.1 m Pt-dvds xylene solution (13 µL, 0.0013 mmol) was placed into the flask, and reaction was initiated. The reaction was continued, and it was confirmed by gas chromatography that the quantity of ethanol produced by the ring-closing reaction had reached the expected quantity based on the starting materials. After the reaction was completed, a colorless a transparent liquid (58.2 g) (boiling point: 117-120° C. at 13,300 Pa, yield: 82%, purity: 98% or higher as confirmed by gas chromatography measurement) was obtained by reduced-pressure distillation.

When $^1$H-NMR measurement at 270 MHz was performed for this colorless and transparent liquid, the spectrum shown in FIG. 1 was obtained. The δ values and identifiers thereof were as shown in Table 1. The compound thus obtained was confirmed as having the structure shown below.

TABLE 1

| Measuring Method | δ (ppm) | Identifier |
|---|---|---|
| $^1$H-NMR | 0.7 | 1) |
| | 1.2 | 3), 6) |
| | 1.8 | 2) |
| | 3.8 | 5) |

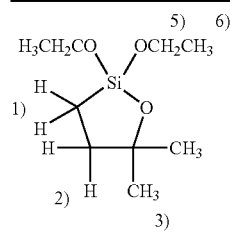

When $^{13}$C-NMR measurement was performed, the spectrum shown in FIG. 2 was obtained. The δ values and identifiers thereof were as shown in Table 2. The compound thus obtained was confirmed as having the structure shown below.

TABLE 2

| Measuring Method | δ (ppm) | Identifier |
|---|---|---|
| $^{13}$C-NMR | 3.88 | 1) |
| | 18.16 | 6) |
| | 29.70 | 3) |
| | 37.43 | 2) |

TABLE 2-continued

| Measuring Method | δ (ppm) | Identifier |
|---|---|---|
| | 59.79 | 5) |
| | 76.25 | 4) |

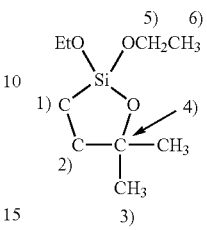

Comparative Example 1

Synthesis was performed in the same manner as in Example 1, except that allyl alcohol was used instead of 2-methyl-3-butene-2-ol. As a result, ten or more types of byproducts were obtained, and the compound could not be purified. (A purity of 30% was confirmed by gas chromatography measurement.)

Hereinafter, the present invention 2 will be described in detail using Examples.

Example 2

Synthesis of Organic Silicon Resin

DESMBO (49 g, 240 mmol), methyltriethoxysilane (78.6 g, 441 mmol), hexamethyldisiloxane (19.5 g, 120 mmol) and acetone (91 g) were charged into and stirred in a reaction vessel provided with a dropping funnel and a magnetic stirrer. Subsequently, 1.5 wt % aqueous solution of hydrochloric acid (37.4 g) was incorporated into the dropping funnel and slowly dripped. After dropping was completed, stirring was conducted for 1.5 hours at room temperature. Diisopropyl ether (200 g) was then added, anhydrous magnesium sulfate was added to dehydrate for two hours. The anhydrous magnesium sulfate was filtered out, and hexamethyldisilazane (38.7 g, 240 mmol) was slowly added while stirring. After two hours of stirring at room temperature, the solvent was evaporated under reduced pressure. After that, methylethylketone (200 g) and a 1N aqueous solution of hydrochloric acid were added to rinse the product, rinsing with water was repeated until the water layer was neutralized. The product was dehydrated by anhydrous magnesium sulfate, and the solvent was evaporated under reduced pressure to obtain an organic silicon resin (73.3 g, 89%).

When $^1$H-NMR measurement at 270 MHz was performed for this organic silicon resin, the spectrum shown in FIG. 3 was obtained.

The δ values and identifiers thereof were as shown in Table 3. The compound thus obtained was confirmed as having the structure shown below.

TABLE 3

| Measuring Method | δ (ppm) | Identifier |
|---|---|---|
| $^1$H-NMR | 0.1 | 1) |
| | 0.6 | 2) |
| | 1.2 | 3) |

TABLE 3-continued

| Measuring Method | δ (ppm) | Identifier |
|---|---|---|
| | 1.5 | 4) |
| | 2.8 | 5) |

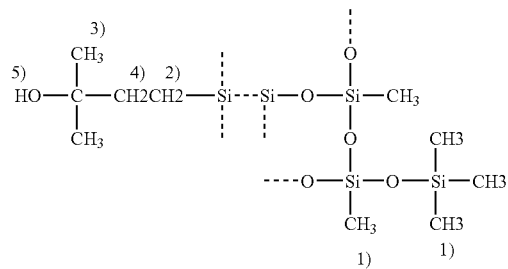

When $^{13}$C-NMR measurement was performed, the spectrum shown in FIG. 4 was obtained.

The δ values and identifiers thereof were as shown in Table 4. The compound thus obtained was confirmed as having the structure shown below.

TABLE 4

| Measuring Method | δ (ppm) | Identifier |
|---|---|---|
| $^{13}$C-NMR | 1.63 | 1) |
| | 7.12 | 2) |
| | 28.54 | 3) |
| | 36.86 | 4) |
| | 71.29 | 5) |

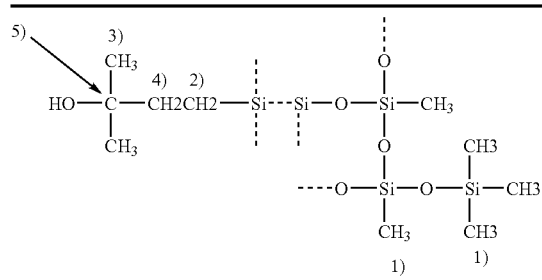

When IR measurement was performed, the spectrum shown in FIG. 5 was obtained. An O—H stretching vibration was observed at 3,400 cm$^{-1}$, and the presence of an alcoholic hydroxyl group was confirmed.

Example 3

Stability Test

Propylene glycol methyl ether acetate containing 0.5 wt % of water was prepared as the solvent. The organic silicon resin produced in Example 1 was dissolved to a concentration of 10 wt % in the solvent, and a sample was created. This sample was allowed to stand at 60° C. for three days, and the change in molecular weight was monitored. The results are shown in Table 5.

TABLE 5

| Days | Mw | Mn | Mw/Mn |
|---|---|---|---|
| 0 | 3,400 | 2,700 | 1.3 |
| 1 | 3,300 | 2,600 | 1.3 |

TABLE 5-continued

| Days | Mw | Mn | Mw/Mn |
|---|---|---|---|
| 2 | 3,400 | 2,700 | 1.3 |
| 3 | 3,300 | 2,600 | 1.3 |

It was confirmed that the organic silicon resin was stable, having no change in molecular weight.

Comparative Example 2

A Case in which the Terminal Silanol of the Resin was not Terminated 1,1-Diethyl-5,5-dimethyl-1-sila-2-oxacyclopentane (49 g, 240 mmol), methyltriethoxysilane (78.6 g, 441 mmol), hexamethyldisiloxane (19.5 g, 120 mmol) and acetone (91 g) were charged into and stirred in a reaction vessel provided with a dropping funnel and a magnetic stirrer. Subsequently, 1.5 wt % aqueous solution of hydrochloric acid (37.4 g) was incorporated into the dropping funnel and slowly dripped. After dropping was completed, stirring was conducted for 1.5 hours at room temperature. When the solvent was evaporated under reduced pressure, the product gelled.

INDUSTRIAL APPLICABILITY

The production method of the present invention 1 is useful as a technique for inexpensively producing a cyclic organic silicon compound having an alcoholic hydroxyl group and an alkoxyl group, protected by an organic substituent group.

The cyclic organic silicon compound obtained by the present invention 1 is useful as a starting material for a resist which is used in lithography.

The organic silicon resin having an alcoholic hydroxyl group of the present invention 2 is useful as a starting material for lithographic material, organic-inorganic hybrid material and the like.

Figure 1:
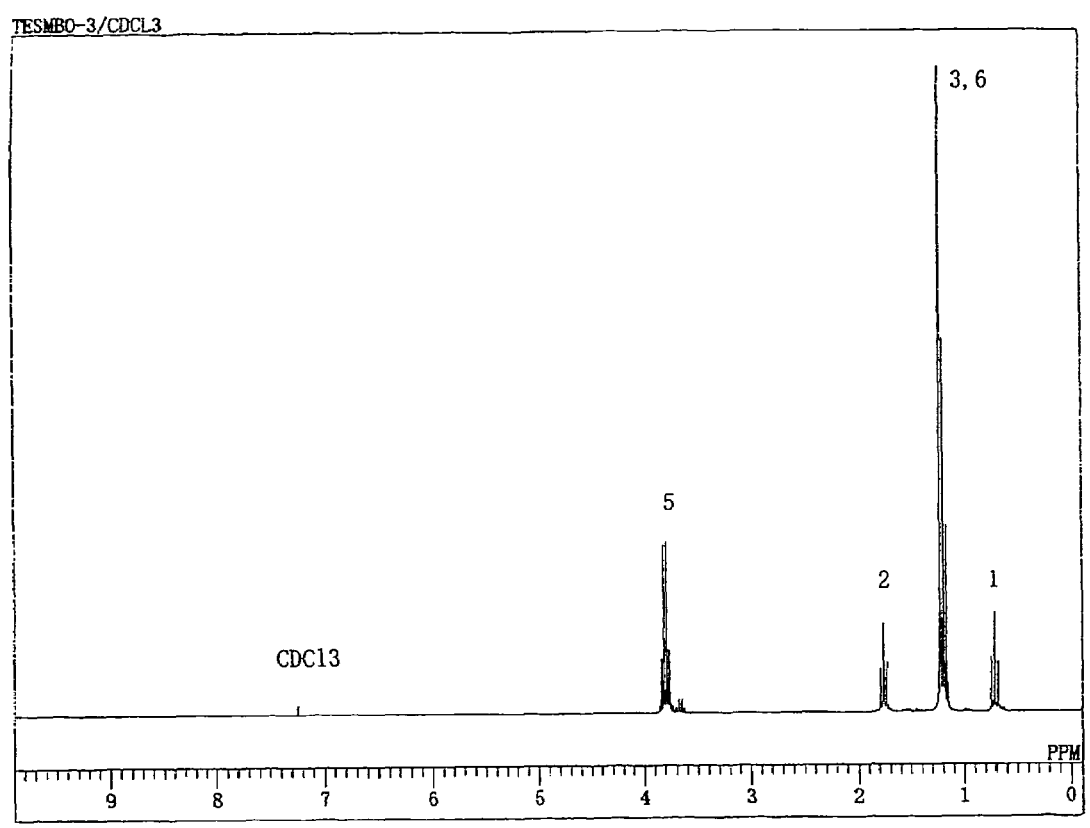
FIG. 1 is $^1$H-NMR spectrum of the compound obtained in Example 1.
Figure 2:
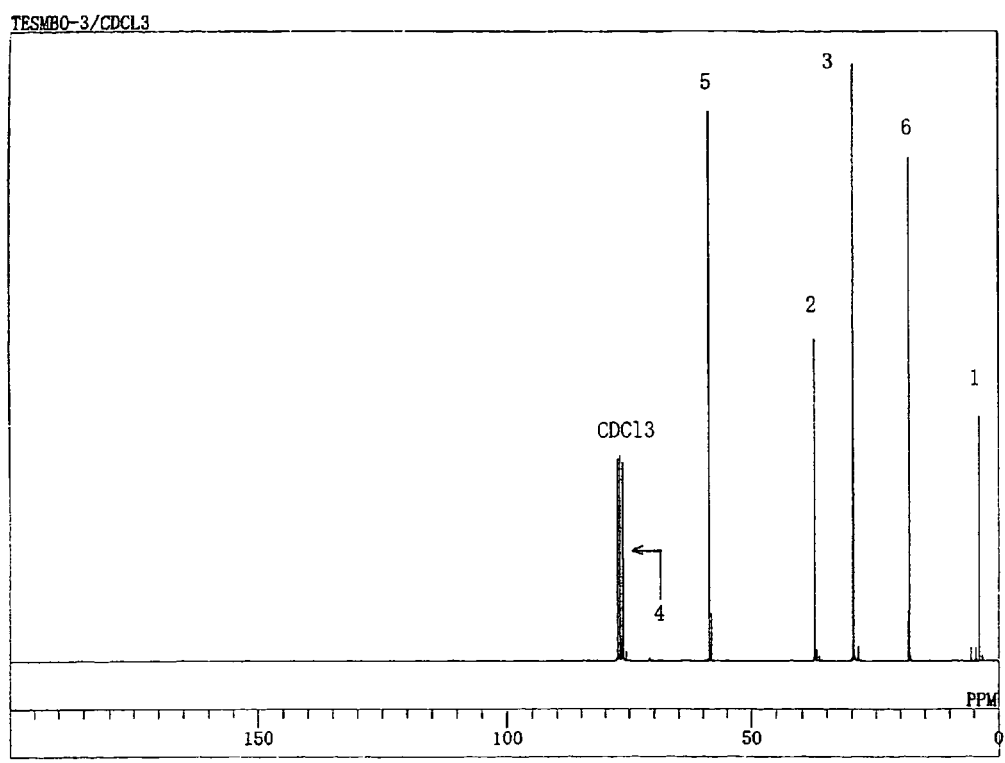
FIG. 2 is $^{13}$C-NMR spectrum of the compound obtained in Example 1.
Figure 3:
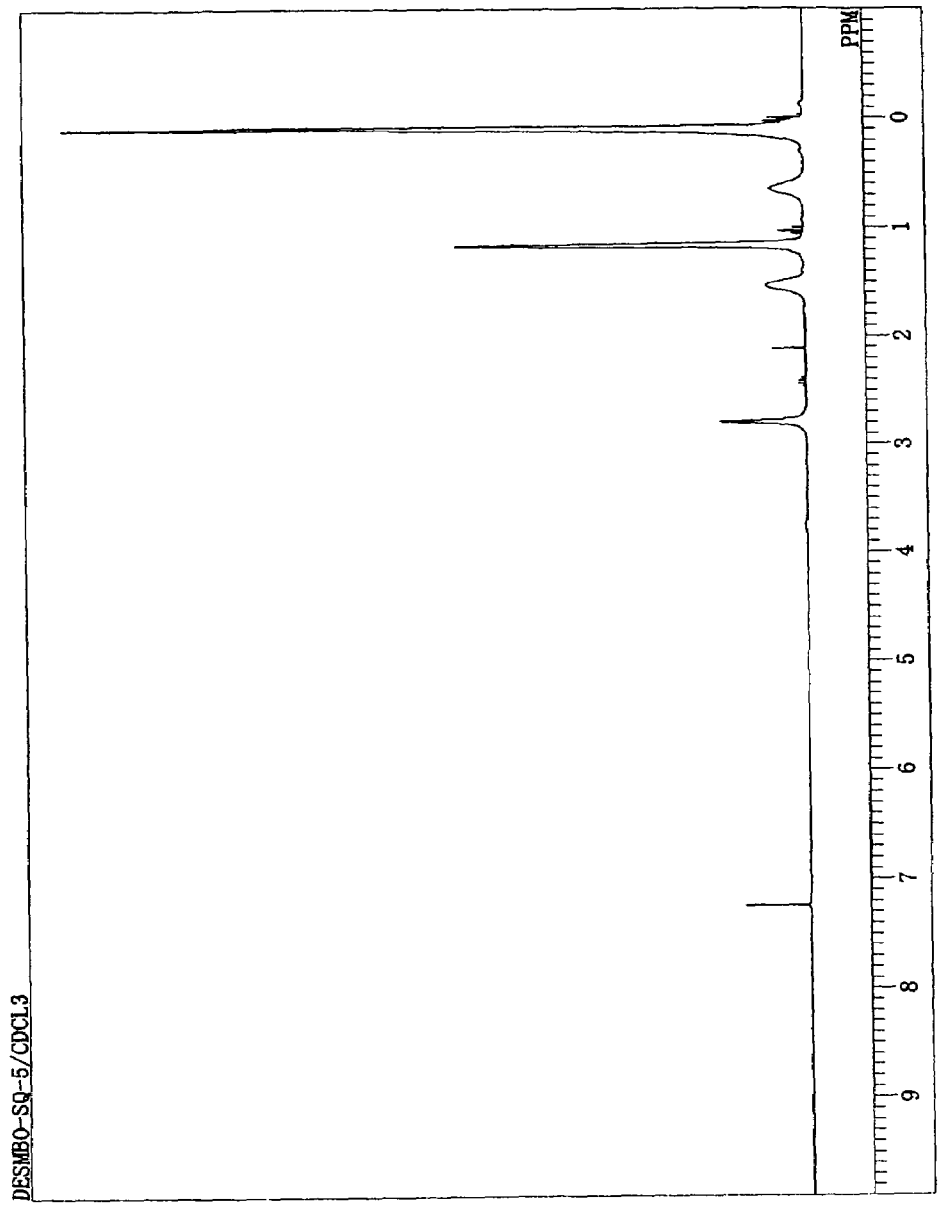
FIG. 3 is $^1$H-NMR spectrum of the organic silicon resin obtained in Example 1.
Figure 4:
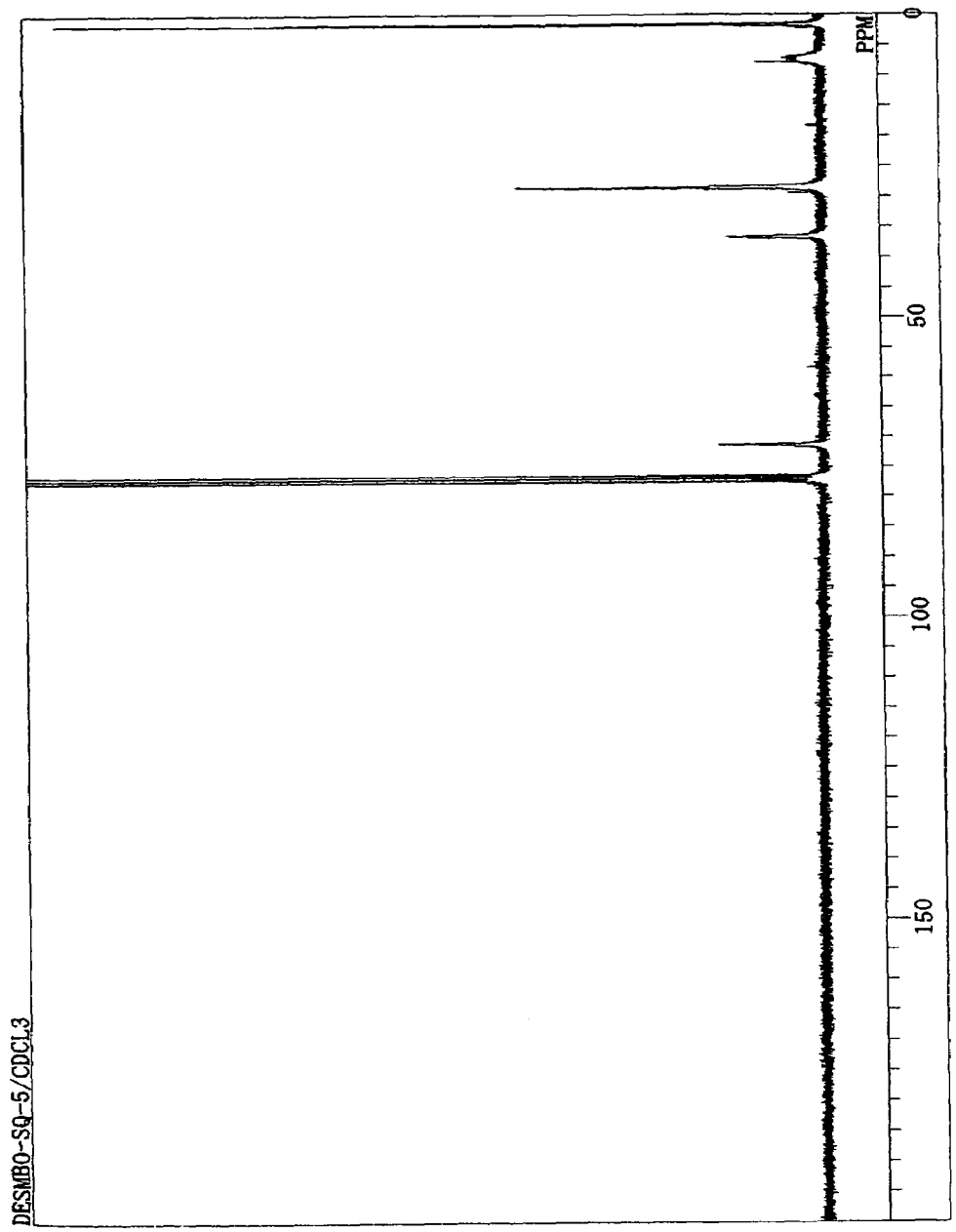
FIG. 4 is $^{13}$C-NMR spectrum of the organic silicon resin obtained in Example 1.
Figure 5:
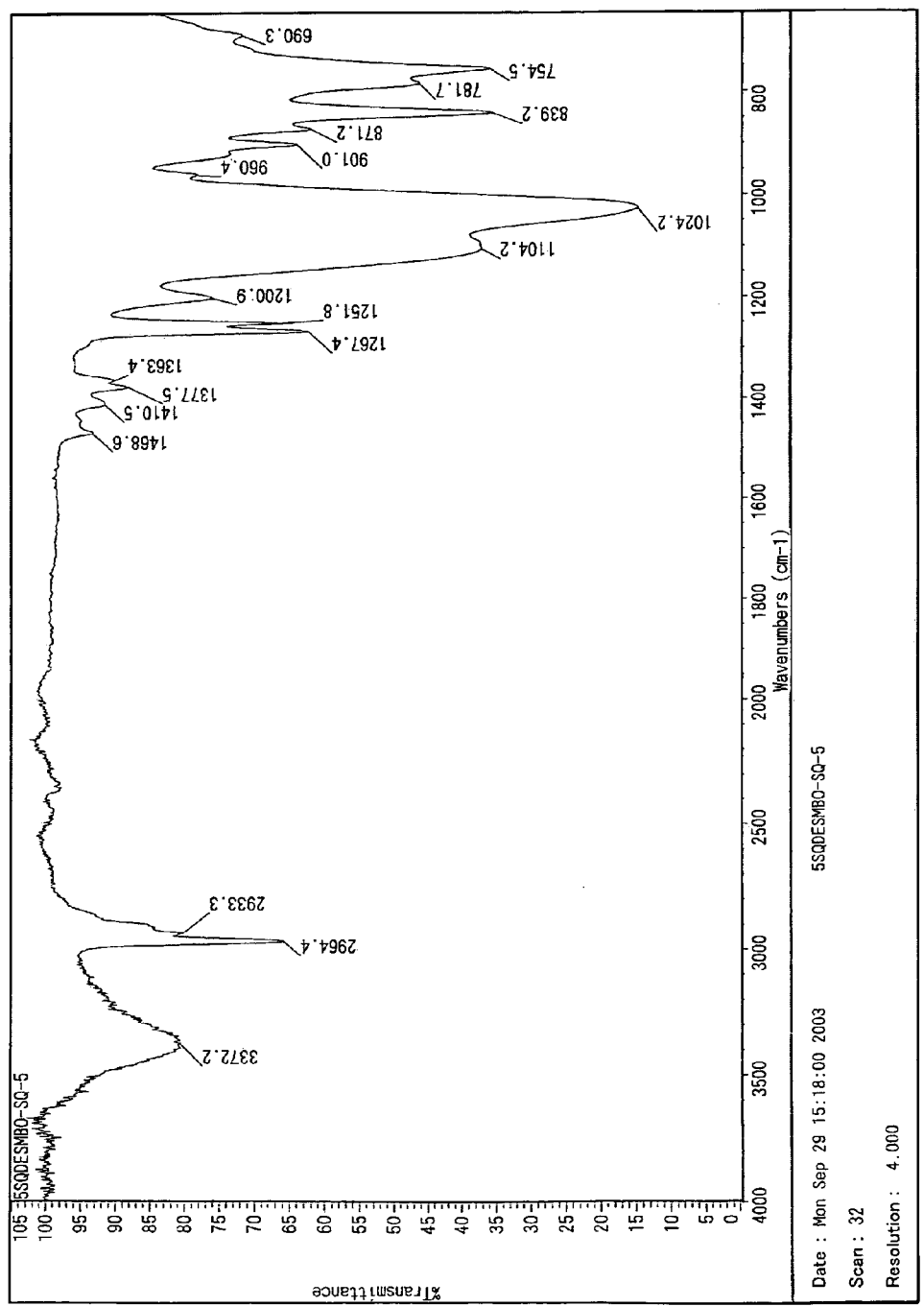
FIG. 5 is IR spectrum of the organic silicon resin obtained in Example 1.

The invention claimed is:

1. A method for producing a cyclic organic silicon compound represented by the general formula (3) below, comprising reacting an olefin represented by the general formula (1) below and an alkoxysilane represented by the general formula (2) below in the presence of a catalyst comprising a transition metal;

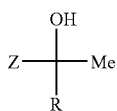

(1)

wherein:
- Z is alkenyl group having carbon atoms from 2 to 5 where the terminal carbon atom $C_E$ distant from the carbon atom to which the hydroxyl group is bonded forms a carbon-carbon unsaturated bond;
- R is methyl group or hydrogen atom; and
- Me is methyl group;

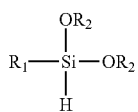

(2)

wherein:
- $R_1$ is alkyl group or alkoxyl group, having carbon atoms from 1 to 3;
- $R_2$ is alkyl group having carbon atoms from 1 to 3; and the plurality of $R_2$ may be the same as or different from each other; and

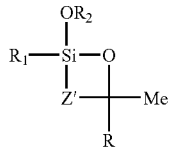

(3)

wherein:
- Z' is alkylene group having carbon atoms from 2 to 5, wherein said carbon-carbon unsaturated bond in said Z transformed into a saturated bond and said terminal carbon atom $C_E$ in said Z binds to Si atom;
- R is methyl group or hydrogen atom;
- $R_1$ is alkyl group or alkoxyl group, having carbon atoms from 1 to 3; and
- $R_2$ is alkyl group having carbon atoms from 1 to 3.

2. An organic silicone resin having an alcoholic hydroxyl group, which is obtained by performing hydrolysis and condensation of a cyclic organic silicon compound represented by the general formula (3) below, or of a mixture of the cyclic organic silicon compound and a polyfunctional alkoxysilane,

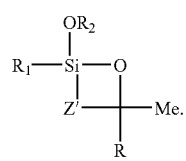

(3)

3. A method for producing an organic silicone resin having an alcoholic hydroxyl group, comprising performing hydrolysis and condensation of a cyclic organic silicon compound represented by the general formula (3) below, or of a mixture of said cyclic organic silicon compound and a polyfunctional alkoxysilane in an organic solvent while maintaining a concentration of a producing polymer at 30% by weight or less,

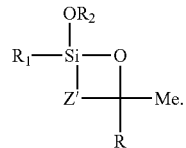

(3)

* * * * *